United States Patent [19]

Heinz

[11] 4,173,142
[45] Nov. 6, 1979

[54] ROTARY VISCOMETER

[76] Inventor: Werner Heinz, Dabringhauser Str. 72, D-5000 Köln-Dellbruck, Fed. Rep. of Germany

[21] Appl. No.: 891,138

[22] Filed: Mar. 28, 1978

[30] Foreign Application Priority Data

Jul. 22, 1977 [DE] Fed. Rep. of Germany ....... 2733099

[51] Int. Cl.² ........................................... G01N 11/10
[52] U.S. Cl. .......................................... 73/60; 73/843
[58] Field of Search .................. 73/59, 60, 101, 15.6, 73/843

[56] References Cited

U.S. PATENT DOCUMENTS 2,752,778  7/1956  Roberts et al. .......................... 73/60

FOREIGN PATENT DOCUMENTS 2149720  4/1973  Fed. Rep. of Germany .............. 73/60
1365677  9/1974  United Kingdom ........................ 73/60
 433381  6/1975  U.S.S.R. ................................... 73/59

OTHER PUBLICATIONS

Morozov et al., *Rheogoniometer for Meas. of Viscoelastic Properties,* Ind. Labs. 38(11), pp. 1780–1782, Nov. 1972.
Borisov et al., *Attachment for Rotational Viscometer,* Ind. Labs. 41(6), pp. 901–902, Jun. 1975.
Raha, *Apparatus to Meas. Dynamic Viscoelasticity of Polymer,* in Journ. of Sci. Instr. 2(1), pp. 1109–1112, Nov. 1968.

*Primary Examiner*—Gerald Goldberg
*Assistant Examiner*—Joseph W. Roskos
*Attorney, Agent, or Firm*—Colton & Stone, Inc.

[57] ABSTRACT

A rotary viscometer is described in which the force measuring device for measuring the force acting on a measuring surface, normal to the surface thereof, is contained within a separate housing releasably connected to the remainder of the apparatus.

The force measuring device comprises a beam and the force is communicated to the beam by an intermediate thrust member which is stiff and does not yield to axial loads but will move readily to other directions to accommodate misalignment.

10 Claims, 2 Drawing Figures

ROTARY VISCOMETER

FIELD OF INVENTION

The invention relates to rotary viscometers operating on the plate to cone or plate to plate principle.

BACKGROUND TO THE INVENTION

In such devices, the plate and cone (or plate and plate), are arranged one above the other and form the two measuring surfaces. Between them is located the substance whose viscosity is to be measured. When the two surfaces are counter-rotated relative to each other, one or both the surfaces being driven, at least one of these surfaces cleaves or slices through the substance to be measured.

A slicing-through action in visco-elastic substances causes not only tangential but also normal forces to occur which tend to force the two surfaces apart. To determine these normal forces, typically the force acting on the lower measuring surface is measured. This surface is either the plate or the cone and may be driven or stationary. High-polymer substances and their solutions belong to the group of visco-elastic substances. One example is the polymers used to produce fibres. After they emerge through the nozzles of an extruder the substance expands perpendicular to its elongated direction, i.e. its direction of stress. The forces which cause this expansion are determined in the rotary viscometer by the device for measuring these normal forces.

PRIOR ART

The rheological properties which are being measured by this device show a strong dependence on temperature. To obtain more accurate and reproducible results, the measuring surfaces are therefore brought up to a specific temperature and in known rotary viscometers they are located for this reason inside a heating chamber and the temperature of the visco-elastic substance to be measured which flows into the chamber is thermostatically controlled.

Additionally in known rotary viscometers the device for measuring the normal force is arranged below the lower measuring surface in the housing of the apparatus, and is a completely integral component part of the viscometer, remaining permanently in place during operation of the appliance. The filling of the measuring chamber containing the two measuring surfaces with a visco-elastic substance, the cleaning, and also the occasional replacement of a measuring surface, must all therefore be carried out from the side, and for this purpose the heating chamber has hitherto been constructed in an expensive manner, in two halves, which are hinged open to permit work to be carried out therewithin. After a heating chamber of this kind has been reassembled the hot air contained in the chamber is relied on to re-heat the measuring surfaces. Owing to the poor thermal conductivity of air, this leads to widely known disadvantages.

OBJECT OF THE INVENTION

It is an object of the present invention to provide an improved rotary viscometer which does not suffer from the aforementioned disadvantages.

THE INVENTION

According to the invention this object is achieved by a rotary viscometer operating on the plate to cone or plate to plate principle constructed in the form of a first assembly comprising:

(1) a chamber containing a substance whose viscosity is to be measured, (2) means for heating same, (3) upper and lower counter rotating measuring surfaces within the chamber, and (4) a torque measuring device for measuring the tangential force exerted on one of the said measuring surfaces;

and a second assembly, comprising:

(1) a housing, (2) a releasable connection between the housing and the first assembly, (3) a force measuring device located within the housing for measuring the force acting normal to one of the said measuring surfaces, and (4) means for transmitting force from the measuring surface for which the normal force acting thereon is to be measured, to the said force measuring means.

By employing such a form of construction it is possible, before each filling or cleaning the appliance or before replacement of a measuring surface, for the operator to remove the separate housing containing the normal-force measuring device and thereafter to remove the measuring surfaces. Where the separate housing is situated below the heating chamber the measuring surfaces can be removed out of the appliance downwards.

Accordingly, the heating chamber need no longer be made so that it can be dismantled. This means that the heating of the measuring surfaces can therefore be effected by means of a heating chamber constructed basically as a liquid bath, which affords more favourable heating of the substance to be measured, due to the better thermal conductivity of liquids.

The arrangement of the normal force measuring device in its own housing, separate from the actual viscometer assembly, also has the advantage that this device does not have to be added to the viscometer as a complementary part until the course of rheological measurements indicates the necessity for observing the normal force. The acquisition and installation of a viscometer embodying the invention can therefore be made on an add-on-unit construction basis.

In a further development of the invention it is proposed that the releasable connection between the housing for the normal force measuring device and the remainder of the apparatus is a screw connection. For example, a lower housing can terminate at its upper end face in a tubular threaded connecting piece, which can be screwed into a complementary screw-threaded aperture in the lower end face of the heating chamber.

It is further proposed that the measuring element inside the housing for measuring the normal force should be a single or double bending beam made of steel or a similar material and the bending is detected by means of strain gauges. In order to exclude the influence of temperature variation, the strain gauges are preferably connected as a full bridge, and the bending beam is dimensioned so that its deflection due to the influence of the normal forces is very small.

The measuring element arranged in the housing should measure the normal forces acting on the lower measuring surface. These forces act from the top downwards along the central axis of the measuring surface. Misalignment between the lower measuring surface and the housing for the normal force measuring device or the effective point of application of the force on the measuring element are usually unavoidable, due to the fact that the connection between the housings is releasable and due to production tolerances. This misalignment allows additional lateral forces to arise on the measuring element when there is a rigid connection between the measuring surface and the measuring element and this is particularly so if the lower measuring surface is the rotating surface. Lateral forces on the measuring element produce measuring errors.

According therefore to a further feature of the invention, the force transmitting element between the lower measuring surface and the measuring element comprises an intermediate thrust element which is rigid to, and transmits axial forces, but can move freely in all other directions. The intermediate thrust element may therefore be made in the form of a cross-coupling or in the form of a conical bearing. If the lower measuring surface rotates, the bearing points of the conical bearing have to be made of a suitable bearing metal, for example, of sintered bronze with molybdenum disulphide.

With rotary viscometers operating on the plate to plate or plate to cone principle, the adjustment and measurement of the distance between the measuring surfaces in the measuring chamber is important. The normal force acting on the lower measuring surface is conducted through the measuring element to the mass of the apparatus. According to another feature of the invention, a micrometer device is located under the measuring element in the lower part of the housing for the normal force measuring device, by which the measuring element and, via the intermediate element, the lower measuring surface as well, can be moved in the axial direction. This makes it possible to accurately adjust and measure the distance between the two measuring surfaces, within wide limits as desired, and to carry out the measurement of the normal force at these known distances.

Normal force measurements are particularly important on molten high polymers, as these have marked visco-elastic characteristics. In this instance, high measuring temperatures are used, which have to be imparted to the polymer by the heating chamber. Force measurement with strain gauges is also influenced by temperature variations when using electrical compensation circuits and therefore according to a further feature of the invention it is proposed that the housing should be at least in part formed with a double wall with inlet and outlet connections, so that a cooling fluid can be passed between the inner and outer walls, such as for example, mains water or heating fluid the circulation of which is controlled by a thermostat. Heat penetrating from the heating chamber via the screw connection and also from the measuring surface via the intermediate thrust element into the housing containing the normal-force measuring and thence into the measuring element itself, is thereby at least in part conducted away, so that the operating temperature of the strain gauges is kept within a range which can be accommodated by the electrical compensation circuits. Flexible ducting is then fitted to the various parts of the apparatus to connect same after assembly, or removed before dismantling.

The normal forces tend to force the upper measuring surface, a cone or a plate, upwards but during the measuring process the distance between the two measuring surfaces must be exactly maintained. In known rotary viscometers the shaft which carries the upper measuring surface and on which the torque is measured, is mounted in radial ball bearings. However, such bearings are not sufficiently rigid in the axial direction and do not hold the shaft exactly. To obtain a rigid mounting in the axial direction, therefore, the invention also provides that in addition to the radial bearings, bearings are provided which are rigid in the axial direction, for example, axial ball bearings or thrust bearings.

The invention will now be described by way of example with reference to the embodiment of the invention shown in the drawings.

In the drawings

FIG. 1 is a side view, partly in section, of the rotary viscometer according to the invention, and FIG. 2 is a side view of part of the viscometer of FIG. 1 as seen in the direction of the arrows at the ends of the line II—II in FIG. 1.

DESCRIPTION OF EMBODIMENT

Figure 1:
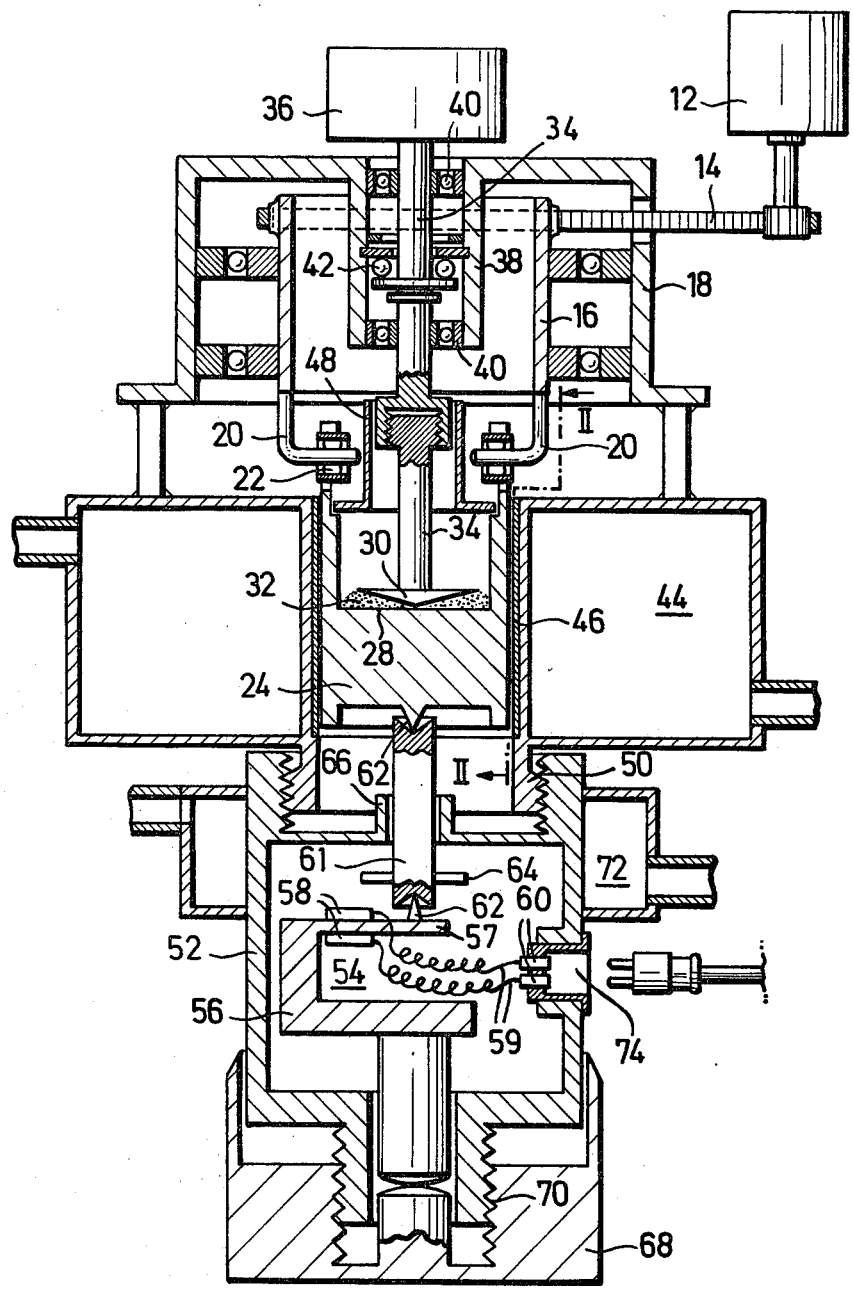
Figure 2:
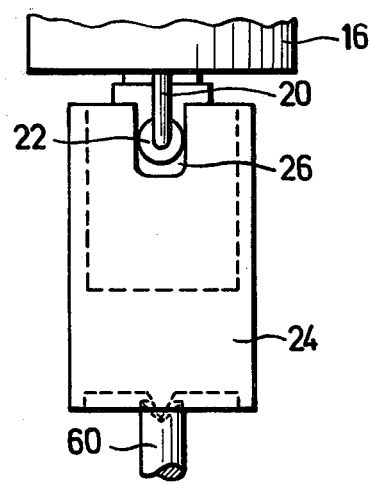

A regulated disc rotor D.C. motor 12, drives the torque shaft 16 via a toothed belt 14. The torque shaft 16 is mounted in a bell housing 18. At the lower end of the torque shaft 16 there are two right-angled carrier arms 20. These engage in small ball bearings 22. See also FIG. 2. In its upper edge the cylinder 24, in which the acutal measuring is carried out, has two parallel-sided slots 26 in which the ball bearings 22 are located. In this way the rotary movement of the torque shaft 16 is transmitted to the cylinder 24, but due to the ball bearings 22, the cylinder 24 is free to move axially freely and can carry out axial movements readily. This is true despite the tangential pressure of the ball bearings 22 on the walls of the slots 26 in which they are accommodated and which is required to transmit rotary movement to the cylinder 24. This easy movement of the cylinder in the axial direction means that it can perform axial movements occasioned by the normal forces to be measured with the minimum of frictional resistance and therefore with a high degree of accuracy of measurement.

The cylinder 24 contains a flat surface 28 which forms a lower, plate-measuring surface. An inverted cone 30 lies above the surface 28 and forms the upper measuring surface. The substance 32 the viscosity of which is to be measured fills the wedge-shaped gap between the two measuring surfaces. When the cylinder 24 is rotated and with it the surface 28, the substance 32 is subjected to slicing and sweeping movements which produce tangential and normal forces to arise on the measuring surfaces. The tangential forces are transmitted to the cone 30 which is free to rotate. The cone 30 is fixed to the lower end of the measuring shaft 34 and the latter is mounted in a plurality of bearings and at its upper end comprises the input to a torque measuring device 36.

In the bell housing 18 there is a tubular inner housing 38 in which are located the bearings which hold the measuring shaft 34. As shown there are two radial ball bearings 40 and one axial thrust ball bearing 42.

The cylinder 24 which incorporates the lower measuring surface 28 is arranged inside a heating chamber 44. This is connected via pipe connections to a liquid heating circuit in which the circulation is controlled by a thermostat. A sleeve 46 made of a bearing metal with high thermal conductivity ensures a good heat transfer from the bath of liquid in the heating chamber 44 to the measuring surface 28 via the mass of the metal cylinder 24 located between them. A cover 48 inverted over the cone 30 prevents radiation and convection of heat away upwards. This prevents heat loss. A good heating of the substance 32 to be measured is thus assured.

With good machining of the cylinder 24 within the sleeve 46, the frictional resistance to axial movement of the cylinder 24, which occurs during the measurement of normal force, is slight. It is particularly small when the cylinder 24 is rotated since then there is no static friction.

The heating chamber 44 terminates at the bottom in a screw thread 50. The housing 52 which contains the device for measuring the normal force is screwed on to this. The normal force acting on the lower measuring surface 28 is measured with the force measuring device 54. This consists mainly of a bending beam 56 made of steel, including a horizontal portion 57 with strain gauges 58 stuck to it. Leads 59 connect the gauges 58 to sockets 60 in which a plug is inserted for operation. A rod 61 made of bearing metal transmits the normal force acting downwards in the axial direction from the cylinder 24 to the measuring device 54. The rod 61 is mounted top and bottom in pivot bearings 62, and is therefore very rigid to forces which act in the vertical direction. However, in the horizontal direction it yields readily. Misalignment between the cylinder 24 and the measuring device 54 does not enter into the measurement. On the lower end of the rod 61 lateral pins 64 are seated. These prevent the rod 61 from falling out of the housing 52 when this is unscrewed.

A tubular cap 66 on the upper end of the housing 52 surrounds the rod 61, which is thus guided centrally and the engagement of the pivot and the socket of the pivot bearing 62 as the housing 52 is screwed onto the thread 50 is facilitated.

At the bottom, the housing 52 is closed off by an adjustment cap 68. This has a fine thread 70 with which it is screwed onto a mating thread on the housing 52. By rotating the adjustment cap 68 the axial distance between the plate and the cone or between the two measurement surfaces 28 and 30 can be set exactly. An annular chamber 72 with fluid inlet and outlet connections encloses the housing 52 and serves to hold its temperature constant by means of a thermostatically controlled liquid flow therethrough. This applies particularly when the heating chamber 44 is required to be brought up to elevated temperatures. The force measuring device 54 is connected via the leads 59, the sockets 60 and a plug connection 74 to an electronic circuit for indicating the measured values.

I claim:

1. A rotary viscometer operating on the plate to cone or plate to plate principle constructed in the form of a first assembly comprising:
    (1) a chamber containing a substance whose viscosity is to be measured,
    (2) means for heating same,
    (3) upper and lower, counter-rotating measuring surfaces within the chamber, and
    (4) a torque measuring device for measuring the tangential force exerted on one of the said measuring surfaces,
and a second assembly, comprising:
    (1) a housing,
    (2) a releasable connection between the housing and the first assembly,
    (3) a force measuring device located within the housing for measuring the force acting normal to one of the said measuring surfaces, and
    (4) means for transmitting force from the measuring surface for which the normal force acting thereon is to be measured, to the said force measuring means.

2. A rotary viscometer as set forth in claim 1 wherein the housing is connected to the said chamber.

3. A rotary viscometer as set forth in claim 1 wherein the releasable connection is a screw connection.

4. A rotary viscometer as set forth in claim 1 wherein the measuring element of the said force measuring device is a beam having strain gauges secured thereto for indicating the deflection of the beam.

5. A rotary viscometer as set forth in claim 1 wherein the means for transmitting force between the measuring surface and the force measuring device comprises an intermediate stiff thrust-transmitting element which does not yield under axial forces but which can move freely in other directions.

6. A rotary viscometer as set forth in claim 5 wherein the intermediate stiff thrust-transmitting element is a rigid rod mounted in pivot bearings at each end.

7. A rotary viscometer as set forth in claim 1 wherein the said force measuring device can be moved relative to the measuring surfaces.

8. A rotary viscometer as set forth in claim 7 further comprising a cap member within which one end of the beam is mounted wherein the cap member is axially displaceable relative to the housing by means of a fine screw threaded engagement between it and the housing.

9. A rotary viscometer as set forth in claim 1, further comprising an annular chamber which circumscribes the housing and through which liquid can be made to flow for heating or cooling the housing.

10. A rotary viscometer as set forth in claim 1 further comprising a rotatable shaft which carries the upper measuring surface at the lower end, and bearing means in the housing through which the shaft passes, at least one of the said bearing means preventing axial movement of the said shaft.

* * * * *